United States Patent [19]
Sittler

[11] Patent Number: 5,855,850
[45] Date of Patent: *Jan. 5, 1999

[54] MICROMACHINED PHOTOIONIZATION DETECTOR

[75] Inventor: Fred C. Sittler, Victoria, Minn.

[73] Assignee: Rosemount Analytical Inc., La Habra, Calif.

[*] Notice: This patent issued on a continued prosecution application filed under 37 CFR 1.53(d), and is subject to the twenty year patent term provisions of 35 U.S.C. 154(a)(2).

[21] Appl. No.: 536,837

[22] Filed: Sep. 29, 1995

[51] Int. Cl.$^6$ .......................... G01N 21/01; G01N 23/12; G01T 1/18; H01J 27/00
[52] U.S. Cl. ................................ 422/98; 422/50; 422/89; 422/90; 436/153; 250/373; 250/382; 250/383; 250/423 P; 250/437
[58] Field of Search ................................... 250/382, 423, 250/423 P, 437, 373, 383; 422/83, 88, 89, 90, 98, 50; 436/153

[56] References Cited

U.S. PATENT DOCUMENTS

| | | | |
|---|---|---|---|
| 5,021,672 | 6/1991 | Parkinson | 250/492.2 |
| 5,126,574 | 6/1992 | Gallagher | 250/492.2 |
| 5,191,217 | 3/1993 | Kane et al. | 250/423 |
| 5,245,192 | 9/1993 | Houseman | 250/423 |
| 5,401,963 | 3/1995 | Sittler | 250/288 |

FOREIGN PATENT DOCUMENTS

| | | |
|---|---|---|
| 290268 | 5/1991 | German Dem. Rep. . |
| 4320607 | 12/1994 | Germany . |
| 2191110 | 12/1987 | United Kingdom . |

OTHER PUBLICATIONS

S. Kapila et al. *J. Chromatog.* 1983, 259, 205–210.
W. Nutmagul et al. *Anal. Chem.* 1983, 55, 2160–2164.
J.N. Davenport et al. *J. Chromatog.* 198, 290, 13–32.
S. Yamada et al. *Anal. Chim. Acta* 1984, 156, 273–277.
N.J. Barker et al. *Anal. Instrum.* 1985, 21, 171–179.
R.A. Mowry Jr. *Anal. Instrum.* 1986, 22, 13–26.
J.N. Driscoll *Am. Lab.* 1986, 18, 95–101.
G. Arnold et al. *Symp. Biol. Hung.* 1988, 37, 23–30.
A. Manz et al. *Trends Anal. Chem.* 1991, 10, 144–149.
S. Yamada *Anal. Chem.* 1991, 63, 1894–1897.
M. Suda et al. *Appl. Biochem. Biotechnol.* 1993, 41, 3–10.
R.R. Reston et al. *Proc.—Electrochem. Soc.* 1993, 93–7, 577–588.
R.R. Reston et al *J. Microelectromech. Syst.* 1994, 3, 134–146.
Y. Murakami et al. *Electroanalysis* 1994, 6, 735–739.
W.E. van der Linden *Spec. Pub.—R. Soc. Chem.* 1994, 154 228–235.
"Journal of Chemistry of the USSR", The Limiting Performance of a Flame Automic–Ionization Spectrometer, by, A.G. Marunkov and N.V. Chekalin, Russian Original vol. 42, No. 4, Part 1, Apr., 1987, Sep. 20, 1987, Plenum Publishing Corporation, pp. 506–508.

*Primary Examiner*—Arlen Soderquist
*Attorney, Agent, or Firm*—Westman, Champlin & Kelly, P.A.

[57] ABSTRACT

A photoionization detector includes a brittle substrate having a void micromachined therein with a void inlet and a void outlet. First and second electrodes are disposed in the void. An ultraviolet transparent member covers at least a portion of the void in which the electrodes are disposed. A gas sample passes through the void and is exposed to ultraviolet radiation from a UV source. Ionization of the sample is measured as current flowing between the electrodes.

7 Claims, 2 Drawing Sheets

MICROMACHINED PHOTOIONIZATION DETECTOR

BACKGROUND OF THE INVENTION

The present invention deals with an ionization detector. More specifically, the present invention deals with a photoionization detector formed on a brittle substrate.

Photoionization detectors are used to detect certain gas species. A gas sample is passed through a chamber with two electrodes disposed in the chamber. A substantial voltage is applied across the chamber and a current detection device is connected in the electrical circuit containing the electrodes.

The chamber is illuminated by ultraviolet (UV) radiation as the gas is passing through the chamber. Certain gas species are ionizable when radiated with UV radiation. If one of those species is present in the chamber, it ionizes under illumination by UV radiation. The ions are collected at the negative electrode, and current is thus generated and measured to detect the gas species of interest.

Conventional photoionization detectors are relatively large and are formed of discrete parts.

SUMMARY OF THE INVENTION

A photoionization detector includes a brittle substrate having a void therein. First and second electrodes are disposed in the void. An ultraviolet transparent member covers at least a portion of the void in which the electrodes are disposed. A gas sample passes through the void and is exposed to ultraviolet radiation from a UV source. Ionization of the sample is measured as current flowing between the electrodes.

DETAILED DESCRIPTION OF THE PREFERRED EMBODIMENTS

In the context of this disclosure, the term "micromachined" used in connection with a device refers to a device the fabrication of which can include processes similar to those used in fabricating integrated circuits or silicon micromechanical devices, such as photolithography, chemical etching, electrostatic discharged machining (EDM), vitreous molding, laser machining and other similar processes known to those skilled in the art.

Figure 1:
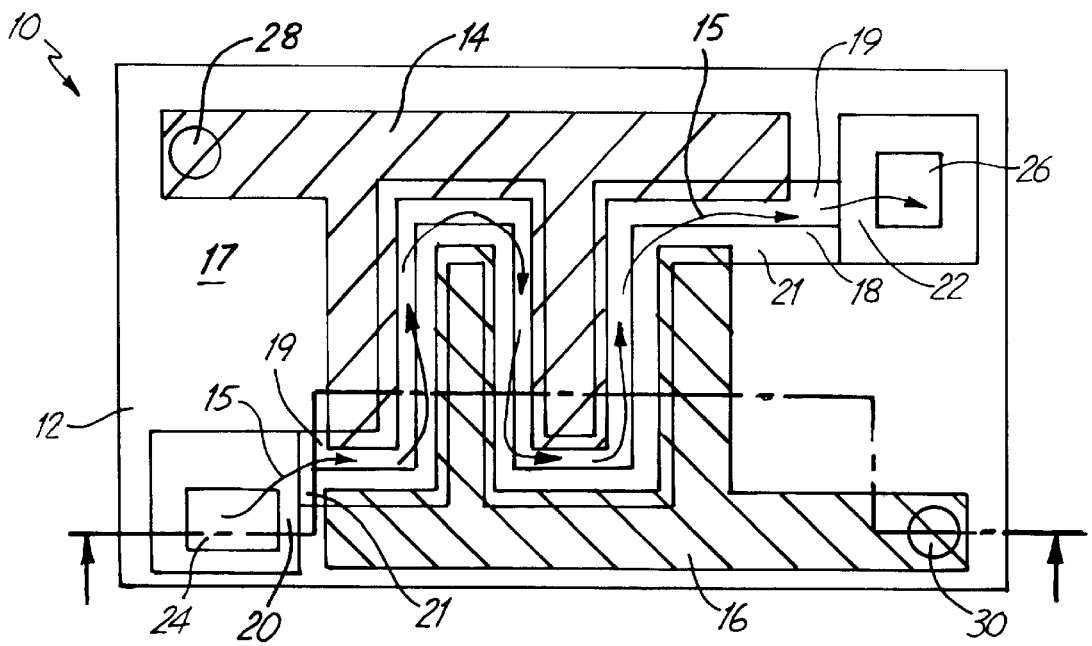
FIG. 1 is a top plan view of a portion of a photoionization detector according to the present invention.

FIG. 1 is a top plan view of photoionization detector 10 according to the present invention. Photo ionization detector 10 includes brittle substrate 12 and first and second electrodes 14 and 16. Detector 10 also includes a UV transparent member (shown in FIG. 2) which is disposed over electrodes 14 and 16.

Brittle substrate 12 can be any suitable brittle substrate which is non-reactive with the gas, such as silicon, gallium arsenide (GaAs), sapphire, alumina, or quartz. In the embodiment shown in FIG. 1, substrate 12 has a first major surface 17 with a void 18 formed therein. Void 18, in FIG. 1, is in the form of a generally serpentine channel micromachined between an inlet end 20 and outlet end 22. Channel 18 is formed by any suitable process, such as etching, and is defined in the embodiment shown in FIG. 1 by two generally opposing side surfaces 19 and 21 which extend away from first major surface 17.

Inlet end 20 and outlet end 22 have apertures 24 and 26, respectively, formed in substrate 12. Gas flow is indicated by arrows 15. In the embodiment shown in FIG. 1, apertures 24 and 26 are formed in a direction normal to the first major surface 17 of substrate 12. However, any other suitable inlet and outlet arrangement can also be used.

Electrode 14, in the preferred embodiment, comprises a metalized film (such as aluminum) deposited on the first major surface 17 of substrate 12 and extends along side surface 19 into channel 18. Electrode 16, in the preferred embodiment, also comprises a metalized film deposited on the first major surface 17 and extends along side 21 into channel 18. Electrodes 14 and 16 are provided with electrical connection pad areas (or pads) 28 and 30. Apertures are formed in the UV transparent member (shown in FIG. 2) to provide electrical access to pads 28 and 30 on electrodes 14 and 16, respectively.

Figure 2:
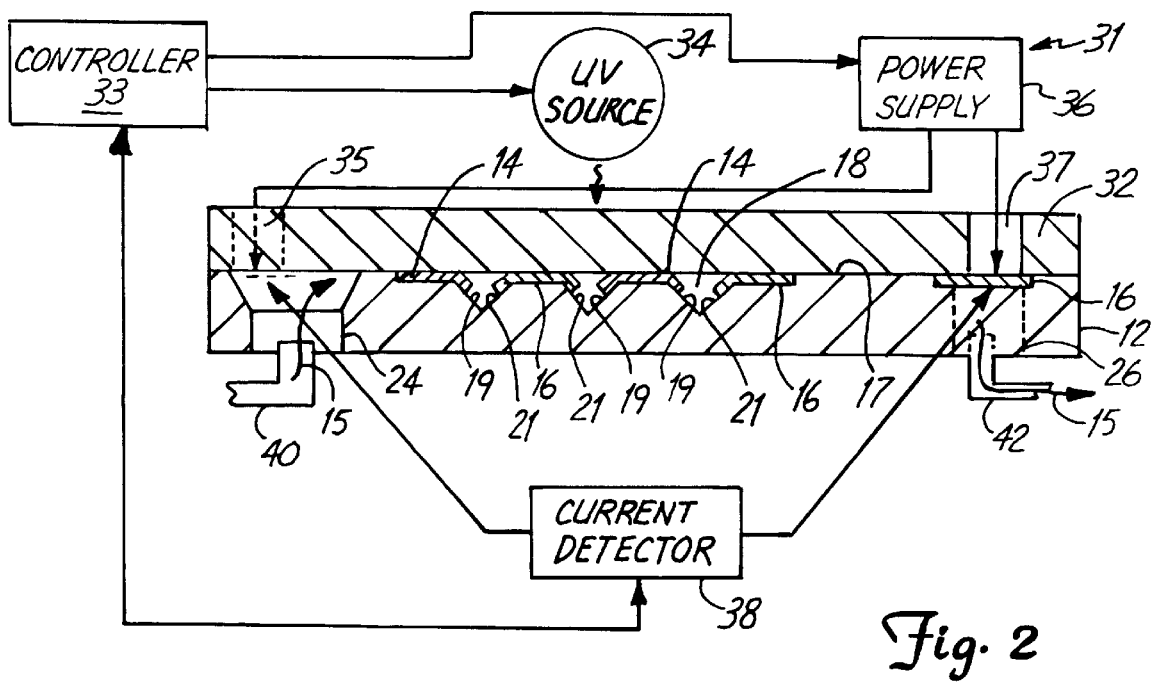
FIG. 2 is a partial side sectional view of a photoionization detection system according to the present invention and shown in partial block diagram form.

FIG. 2 is a side sectional view of a photoionization detection system 31 utilizing photoionization detector 10 according to the present invention. FIG. 2 better illustrates the arrangement of a UV transparent member 32 over substrate 12 and electrodes 14 and 16. Detection system 31 also includes controller 33 (such as a digital computer or other suitable controller), UV source 34, power supply 36 and current detector 38.

In operation, a gas sample is input into detector 10 through inlet aperture 24, and passes through inlet end 20 of channel 18. The gas sample can be provided simply by positive pressure at the gas supply, by a carrier gas, by controller 33 controlling a microvalve to allow the gas sample to enter detector 10, or by any other suitable means.

Gas passes through channel 18 and is expelled, at outlet end 22, through aperture 26. As the gas passes through channel 18, UV source 34 is energized by controller 33. UV source 34 irradiates and the gas sample in channel 18 with ultraviolet radiation. Power supply 36 is coupled through apertures 35 and 37 to pads 28 and 30 on electrodes 14 and 16. Power supply 35 is controlled by controller 33 to apply a voltage across electrodes 14 and 16. Current detector 38 is connected in the electrical circuit which includes electrodes 14 and 16. Under the ultraviolet radiation, components of the gas passing through channel 18 ionizes and charge builds up on electrodes 14 and 16, thus inducing a current to flow between the electrodes. This current is measured by current detector 38, and the gas species of interest is detected in this fashion.

FIG. 2 better illustrates that electrodes 14 and 16 are formed as a metal layer (such as a metalized film), a portion of which is disposed on the first major surface 17 of substrate 12, and a portion of which extends down within channel 18. Electrodes 14 and 16 are preferably disposed on opposite sides of channel 18 so that the electrodes are exposed to a significant portion of the gas travelling through channel 18. UV transparent member 32 sandwiches the portion of the electrodes deposited on the first major surface 17 of substrate 12 between itself and substrate 12. The UV transparent member is preferably quartz, but can be any suitable UV transparent member which is non-reactive with the gas.

FIG. 2 also shows one preferred embodiment of the detection system 31 in which tubes 40 and 42 are used to provide the gas sample under analysis to detector 10. Tubes 40 and 42 need not be used, and appropriate plumbing or other channels can simply be coupled adjacent apertures 24 and 26 to accomplish desired gas flow.

It should be noted that it is desirable to ensure a maximum amount of reaction between the TV radiation and the gas sample under analysis to achieve substantially complete ionization. However, it is also desirable to save space. Therefore, in the preferred embodiment, channel 18 is a serpentine channel so that it has significant length, yet can be formed in a compact area. While channel 18 is shown as a serpentine channel, it is preferably any suitable circuitous channel.

Figure 3:
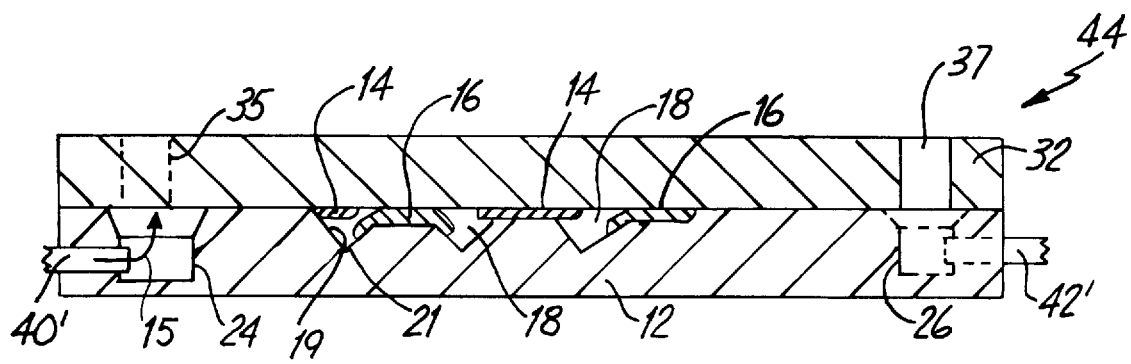
FIG. 3 is a side sectional view of a second embodiment of a photoionization detector according to the present invention.

FIG. 3 is a side sectional view of a second embodiment of a photoionization detector 44 according to the present invention. Detector 44 is similar to detector 10, and similar items are similarly numbered. However, detector 44 has electrode 14 metalized onto UV transparent member 32. This may be less desirable in that electrode 14 acts to block some of the UV radiation from reaching channel 18. Thus, substrate 12 can be formed of a UV transparent material and the UV source 34 can be appropriately repositioned to obtain suitable illumination of channel 18. In such an embodiment, member 32 need not necessarily be UV transparent, but simply a covering member for covering channel 18 and for supporting electrode 14.

In addition, FIG. 3 shows that tubes 40' and 42' are used instead of tubes 40 and 42. In the embodiment shown in FIG. 3, a channel is etched into substrate 12 at both the inlet end 20 and the outlet end 22 of channel 18. A suitable tube is assembled into the channel and adhered to substrate 12 with any suitable adhesive.

Figure 4:
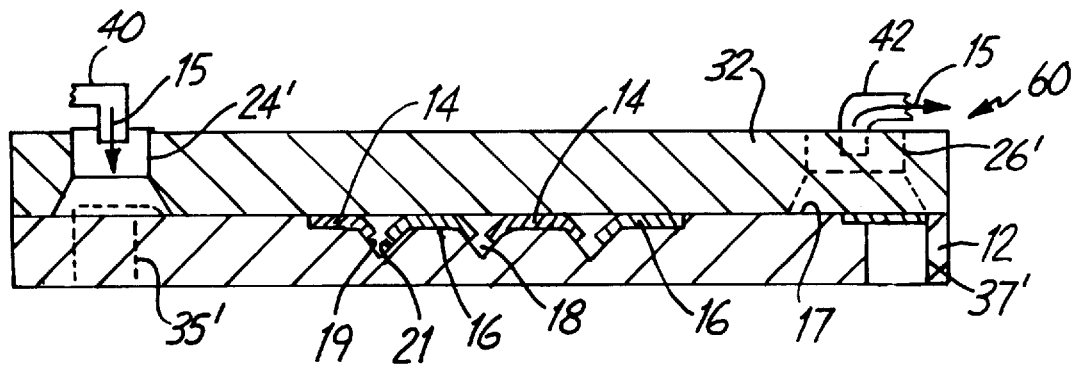
FIG. 4 is a side sectional view of a third embodiment of a photoionization detector according to the present invention.

FIG. 4 shows a side sectional view of a third embodiment of a photoionization detector 60 according to the present invention. Similar items are similar to those shown in FIGS. 1–3. FIG. 4 shows that either the inlet aperture 24 or outlet aperture 26, or both, can alternately be provided as apertures 24' and 26' through UV transparent member 32. In addition, apertures 35 and 37 used to access the electrodes 14 and 16 can also be provided, alternatively, as apertures 35' and 37' through substrate 12, rather than through UV transparent member 32.

Although the present invention has been described with reference to preferred embodiments, workers skilled in the art will recognize that changes may be made in form and detail without departing from the spirit and scope of the invention.

What is claimed is:

1. A photoionization detection system, comprising:
 an ionization detector, comprising:
  a silicon substrate having a major surface and a groove therein, the groove including a first longitudinal sidewall and a second longitudinal sidewall generally opposed to the first longitudinal sidewall;
  a covering member covering at least a portion of the groove to form an elongated chamber, the chamber having an inlet and an outlet, one of the silicon substrate and the covering member being transparent to ultraviolet (UV) radiation;
  a first electrode disposed in the chamber on at least a portion of one of the first longitudinal sidewall, the second longitudinal sidewall, and the covering member; and
  a second electrode disposed in the chamber on at least a portion of another of the first longitudinal sidewall, the second longitudinal sidewall, and the covering member;
 a source of UV radiation positioned to direct UV radiation into the chamber;
 a power supply coupled to the first and second electrodes to apply a voltage across the first and second electrodes; and
 a current detector, coupled to the first and second electrodes, to detect current.

2. The photoionization detection system of claim 1 and further comprising:
 a controller, coupled to the power supply and the source of UV radiation and the current detector.

3. The photoionization detection system of claim 2 wherein the groove comprises a circuitous groove micromachined into the substrate.

4. The photoionization detection system of claim 3 wherein the first electrode comprises a metal layer, and wherein the second electrode comprises a metal layer.

5. The photoionization detection system of claim 4 wherein the first and second electrodes are partially disposed on the first major surface and extend into the circuitous groove along the respective one of first and second longitudinal opposing sidewalls.

6. The photoionization detection system of claim 5 wherein a portion of the first electrode and a portion of the second electrode is disposed between the covering member and the first major surface of the silicon substrate.

7. The photoionization detection system of claim 2 wherein one of the first and second electrodes is disposed on the covering member in the chamber.

* * * * *